(12) United States Patent
Keefe et al.

(10) Patent No.: US 7,371,389 B2
(45) Date of Patent: May 13, 2008

(54) METHODS AND PRODUCTS FOR ENHANCING ENERGY AND NUTRITION IN HUMAN BEINGS

(75) Inventors: Candace R. Keefe, Irvine, CA (US); Michele Arth, Irvine, CA (US)

(73) Assignee: Arbonne International, LLC, Irvine, CA (US)

( * ) Notice: Subject to any disclaimer, the term of this patent is extended or adjusted under 35 U.S.C. 154(b) by 0 days.

(21) Appl. No.: 11/404,237

(22) Filed: Apr. 14, 2006

(65) Prior Publication Data
US 2007/0243210 A1 Oct. 18, 2007

(51) Int. Cl.
*A61K 33/06* (2006.01)
*A61K 36/00* (2006.01)
*A61K 36/73* (2006.01)
*A61K 36/55* (2006.01)
*A61K 36/906* (2006.01)
*A61K 36/87* (2006.01)
*A61K 36/28* (2006.01)

(52) U.S. Cl. .................. 424/195.17; 424/72; 424/682; 424/626; 424/777; 424/765; 424/766; 424/768; 424/774; 424/756; 424/758; 424/760; 424/764; 424/773; 426/474

(58) Field of Classification Search ............... None
See application file for complete search history.

(56) References Cited

U.S. PATENT DOCUMENTS

| | | | | |
|---|---|---|---|---|
| 4,259,358 | A * | 3/1981 | Duthie | 426/46 |
| 6,139,872 | A * | 10/2000 | Walsh | 424/464 |
| 6,323,007 | B1 * | 11/2001 | Moller et al. | 435/74 |
| 6,488,852 | B2 * | 12/2002 | Lucido et al. | 210/610 |
| 7,090,862 | B2 * | 8/2006 | Barrett-Reis et al. | 424/439 |
| 2003/0068365 | A1 * | 4/2003 | Suvanprakorn et al. | 424/450 |
| 2004/0034886 | A1 * | 2/2004 | Cahoon et al. | 800/281 |
| 2004/0082657 | A1 * | 4/2004 | Spiegel | 514/561 |
| 2004/0137094 | A1 * | 7/2004 | Mower et al. | 424/769 |
| 2004/0146539 | A1 * | 7/2004 | Gupta | 424/401 |
| 2004/0156920 | A1 * | 8/2004 | Kane | 424/725 |
| 2004/0253227 | A1 * | 12/2004 | Martin et al. | 424/94.65 |
| 2005/0002992 | A1 * | 1/2005 | McCleary et al. | 424/439 |
| 2005/0008690 | A1 * | 1/2005 | Miller | 424/451 |
| 2005/0100640 | A1 * | 5/2005 | Pearce | 426/89 |

OTHER PUBLICATIONS http://www/marigot.ied/product_range.phtml.*

* cited by examiner

*Primary Examiner*—Susan Hoffman
*Assistant Examiner*—Catheryne Chen
(74) *Attorney, Agent, or Firm*—Patrick F. Bright; Wagner, Anderson & Bright, LLP

(57) ABSTRACT

Methods for increasing energy in men and women include ingesting internally, twice a day, products that include, for women, multivitamins, multiminerals, high-calcium bone support products, high-ORAC super food products, and enzymes, and, for men, multivitamins, multiminerals, prostate support products, high-ORAC super food products, and enzymes.

1 Claim, No Drawings

METHODS AND PRODUCTS FOR ENHANCING ENERGY AND NUTRITION IN HUMAN BEINGS

BACKGROUND OF THE INVENTION

Many nutritional and energy-enhancing products have been disclosed and offered for sale, but none of them adequately supports the human body's ability to efficiently use and create energy. There is a need for a product that provides vitamins, minerals, herbs, enzymes, and superfoods to meet the needs of men and women individually. The methods and products of this invention meet these needs.

SUMMARY OF THE INVENTION

This invention provides products and methods to support a human's body to efficiently use and create energy. These products help meet the needs of men and women individually. These products comprise a plurality of phytonutrient-rich super foods, high-ORAC (oxygen radical absorbance capacity) antioxidants, herb and nutrient combinations, a substance, e.g., bioperine, that supports proper nutrient absorption, and a digestive enzyme mixture that may include proteases, carbohydrates, and lipases. In some embodiments, the men's products comprise two packets to be taken internally, one packet at a time, twice a day. Each packet comprises at least one multivitamin tablet, at least one multimineral tablet, at least one prostate support tablet, at least one high-ORAC super food tablet and at least one enzyme digestive capsule. These products for men support prostate health, vitality and stamina.

For women, in some embodiments, these products comprise two packets to be taken internally, one packet at a time, twice a day. Each packet comprises at least one multivitamin tablet, at least one multimineral tablet, at least one high-calcium bone support tablet, at least one high-ORAC super food tablet, and at least one enzyme digestive capsule. These products for women support healthy bones, urinary tract health, and more. Both the men's and the women's products support energy levels, eye health, immune function, memory and mental performance.

A preferred embodiment of the men's products includes:

Men's MultiVitamin Tablet

| Label Claim | Ingredient Name | Daily Dosage |
|---|---|---|
| 5000 IU | Vitamin A (as beta-carotene bead VG) | 10000.0000 IU |
| 300 IU | Vitamin D (as ergocalciferol) | 600.0000 IU |
| 50 IU | Vitamin E (as d-alpha tocopheryl succinate) | 100.0000 IU |
| 0.06 MG | Vitamin K (as phytonadione) | 0.1200 MG |
| 7.5 MG | Thiamin (as thiamin HCl) | 15.0000 MG |
| 8.75 MG | Riboflavin | 17.5000 MG |
| 15 MG | Niacinamide | 30.0000 MG |
| 12.5 MG | Vitamin B6 (as pyridoxine HCl) | 25.0000 MG |
| 0.05 MG | Vitamin B12 (as cyanocobalamin) | 0.1000 MG |
| 25 MG | Vitamin B5 (as d-calcium pantothenate) | 50.0000 MG |
| 0.3 MG | Folic Acid | 0.6000 MG |
| 87.5 MG | Vitamin C (as Ascorbic Acid) | 175.0000 MG |
| 0.15 MG | Biotin | 0.3000 MG |
| 17.5 IU | Mixed Tocopherols Pwd (35% IU) | 35.0000 IU |
| 25 MG | Gamma-Tocopherol | 50.0000 MG |
| 3 MG | Lutein Bead VG | 6.0000 MG |
| 1.75 MG | Lycopene Bead VB | 3.5000 MG |
| 27.025 MG | Calcium Carbonate | 54.0500 MG |
| 37.5 MG | Maca Root SE (0.6% Macamides) | 75.0000 MG |
| 125 MG | Korean Ginseng Root SE (7% Ginsenosides) | 250.0000 MG |
| 60 MG | *Ginkgo* Leaf SE (24/6) | 120.0000 MG |
| 100 MG | *Rhodiola* Root SE (3% Rosavins/1% Salidroside) | 200.0000 MG |
| 70 MG | Crospovidone | 140.0000 MG |
| 2.5 MG | Black Pepper SE Powder (Bioperine) | 5.0000 MG |

Men's MultiMineral Tablet

| Label Claim | Ingredient Name | Daily Dosage |
|---|---|---|
| 50 IU | Vitamin D (as ergocalciferol) | 200.0000 IU |
| 146.25 MG | Calcium (as calcium carbonate) | 585.0000 MG |
| 150 MG | Magnesium (as magnesium oxide) | 600.0000 MG |
| 5 MG | Zinc (as zinc citrate) | 20.0000 MG |
| 0.05 MG | Selenium (as L-selenomethionine) | 0.2000 MG |
| 0.5 MG | Copper (as copper citrate and sodium copper chlorophyllin) | 2.0000 MG |
| 0.5625 MG | Manganese (as manganese citrate) | 2.2500 MG |
| 0.075 MG | Chromium (as chromium nicotinate) | 0.3000 MG |
| 0.01875 MG | Molybdenum (as molybdenum citrate) | 0.0750 MG |
| 22.5 MG | Potassium (as potassium citrate) | 90.0000 MG |
| 0.25 MG | Boron (as Boron citrate) | 1.0000 MG |
| 0.025 MG | Vanadium (as BMOV) | 0.1000 MG |
| 0.06562 MG | Kelp Pwd | 0.2625 MG |
| 12.5 MG | Aquamin Trace Mineral Complex | 50.0000 MG |
| 12.5 MG | Methylsulfonylmethane Pwd (MSM) | 50.0000 MG |

Men's Prostate Formula Capsule

| Label Claim | Ingredient Name | Daily Dosage |
|---|---|---|
| 320.0000 MG | Saw Palmetto SE | 640.0000 MG |
| 50.0000 MG | Pygeum Bark SE | 100.0000 MG |
| 30.0000 MG | Mixed Phytosterols (40% Beta-Sitosterol) | 60.0000 MG |
| 60.0000 MG | Nettle Root | 120.0000 MG |
| 40.0000 MG | Tomato | 80.0000 MG |
| 40.0000 MG | Spinach | 80.0000 MG |

Men's Super ProFood Blend ™ Tablet

| Label Claim | Ingredient Name | Daily Dosage |
|---|---|---|
| 400 MG | High ORAC Blend (4000 ORAC/ 400 mg) (Green tea leaf extract, quercetin, grape seed extract, rosemary leaf extract) | 800.00 MG |
| 25 MG | Broccoli Sprout | 50.00 MG |
| 25 MG | Parsley Leaf | 50.00 MG |
| 25 MG | Kale Leaf | 50.00 MG |
| 20 MG | Boysenberry Fruit | 40.00 MG |
| 25 MG | Pumpkin Seed | 50.00 MG |
| 20 MG | Raspberry Seed | 40.00 MG |
| 25 MG | Grape Skin SE (25%) | 50.00 MG |
| 25 MG | Blueberry Fruit | 50.00 MG |
| 35 MG | Elderberry Fruit | 70.00 MG |
| 5 MG | Apple Skin SE (5%) | 10.00 MG |
| 50 MG | Citrus Bioflavonoids (50%) | 100.00 MG |
| 20 MG | Pumpkin Fruit | 40.00 MG |
| 50 MG | Pomegranate Fruit SE (5%) | 100.00 MG |
| 30 MG | Red Bell Pepper Fruit | 60.00 MG |
| 30 MG | Tomato Fruit | 60.00 MG |
| 15 MG | Cranberry Fruit | 30.00 MG |

Men's Enzyme Digestive Capsule

| Label Claim | Ingredient Name | Daily Dosage |
|---|---|---|
| 395 MG | Essential Enzyme Blend ™ (Protease, peptidase, amylase, lipase, lactase, cellulose, humecellulase, alpha-galactosidase, glucoamylase, pectinase, invertase, malt diastase phytase) | 790.00 MG |
| 30 MG | Ginger Root SE (5%) | 60.00 MG |
| 25 MG | Peppermint Leaf | 50.00 MG |
| 25 MG | Chamomile Flower PE | 50.00 MG |
| 25 MG | Fennel Seed | 50.00 MG |
| 20 MG | Hawthorn Berry PE (10:1) | 40.00 MG |

A preferred embodiment of the women's products includes:

Women's MultiVitamin Tablet

| Label Claim | Ingredient Name | Daily Dosage |
|---|---|---|
| 5000 IU | Vitamin A (as beta-carotene bead VG) | 10000.0000 IU |
| 300 IU | Vitamin D (as ergocalciferol) | 600.0000 IU |
| 50 IU | Vitamin E (as d-alpha tocopheryl succinate) | 100.0000 IU |
| 0.06 MG | Vitamin K (as phytonadione) | 0.1200 MG |
| 7.5 MG | Thiamin (as thiamin HCl) | 15.0000 MG |
| 7.5 MG | Riboflavin | 15.0000 MG |
| 12.5 MG | Niacinamide | 25.0000 MG |
| 12.5 MG | Vitamin B6 (as pyridoxine HCl) | 25.0000 MG |
| 0.05 MG | Vitamin B12 (as cyanocobalamin) | 0.1000 MG |
| 25 MG | Vitamin B5 (as d-calcium pantothenate) | 50.0000 MG |
| 0.3 MG | Folic Acid | 0.6000 MG |
| 75 MG | Vitamin C (as Ascorbic Acid) | 150.0000 MG |
| 0.2 MG | Biotin | 0.4000 MG |
| 12.5 IU | Mixed Tocopherols Pwd (35% IU) | 25.0000 IU |
| 12.5 MG | Gamma-Tocopherol | 25.0000 MG |
| 3 MG | Lutein Bead VG | 6.0000 MG |
| 0.5 MG | Lycopene Bead VB | 1.0000 MG |
| 44.8 MG | Dicalcium Phosphate | 89.6000 MG |
| 5.6 MG | Andrographis SE | 11.2000 MG |
| 125 MG | Cranberry Fruit | 250.0000 MG |
| 20 MG | Black Cohosh SE Pwd (2.5%) | 40.0000 MG |
| 10 MG | Flax Lignans | 20.0000 MG |
| 25 MG | *Eleuthero* Root SE (0.8%) | 50.0000 MG |
| 20 MG | Crospovidone | 40.0000 MG |
| 2.5 MG | Black Pepper SE Powder (Bioperine) | 5.0000 MG |

Women's MultiMineral Tablet

| Label Claim | Ingredient Name | Daily Dosage |
|---|---|---|
| 100 IU | Vitamin D (as ergocalciferol) | 200.0000 IU |
| 192.5 MG | Calcium (as calcium carbonate) | 385.0000 MG |
| 50 MG | Magnesium (as magnesium oxide) | 100.0000 MG |
| 0 MG | Iodine (from kelp) | 0.0000 MG |
| 7.5 MG | Zinc (as zinc citrate) | 15.0000 MG |
| 0.1 MG | Selenium (as L-selenomethionine) | 0.2000 MG |
| 1 MG | Copper (as copper citrate) | 2.0000 MG |
| 1 MG | Manganese (as manganese citrate) | 2.0000 MG |
| 0.125 MG | Chromium (as chromium nicotinate) | 0.2500 MG |
| 0.0375 MG | Molybdenum (as molybdenum citrate) | 0.0750 MG |
| 37.5 MG | Potassium (as potassium citrate) | 75.0000 MG |
| 1.5 MG | Boron (as Boron citrate) | 3.0000 MG |
| 0.05 MG | Vanadium (as BMOV) | 0.1000 MG |
| 6.25 MG | Silica (from horsetail SE 5%) | 12.5000 MG |
| 37.5 MG | Kelp | 75.0000 MG |
| 25 MG | Aquamin Trace Mineral Complex | 50.0000 MG |
| 25 MG | Methylsulfonylmethane (MSM) | 50.0000 MG |

Women's Calcium Tablet

| Label Claim | Ingredient Name | Daily Dosage | Notes |
|---|---|---|---|
| 112.5 MG | Calcium (as calcium carbonate gran) | 450.0000 MG | |
| 12.5 MG | Calcium (as calcium citrate) | 50.0000 MG | 550 mg Ca |
| 12.5 MG | Calcium (as calcium glycinate) | 50.0000 MG | |
| 87.5 MG | Magnesium (as magnesium oxide gran) | 350.0000 MG | |
| 12.5 MG | Magnesium (as magnesium citrate) | 50.0000 MG | 500 mg |

-continued

Women's Calcium Tablet

| Label Claim | Ingredient Name | Daily Dosage | Notes |
|---|---|---|---|
| 12.5 MG | Magnesium (as magnesium glycinate) | 50.0000 MG | |
| 12.5 MG | Magnesium (as magnesium aspartate) | 50.0000 MG | |
| 5 MG | Cissus | 20.0000 MG | |
| 10 MG | Natural Hops Extract | 40.0000 MG | |
| 0.3504 MG | Copper (as sodium copper chlorophyllin) | 1.4016 MG | |
| 50 IU | Vitamin D (ergocalciferol) | 200.0000 IU | |
| 25 MG | N-Acetyl-L-Cysteine | 100.0000 MG | Assoc. w/bone protection |

Women's Super ProFood Blend ™ Tablet

| Label Claim | Ingredient Name | Daily Dosage |
|---|---|---|
| 400 MG | High ORAC Blend (4000 ORAC/ 400 mg) (Green tea leaf extract, quercetin, grape seed extract, rosemary leaf extract) | 800.00 MG |
| 25 MG | Broccoli Sprout | 50.00 MG |
| 25 MG | Parsley Leaf | 50.00 MG |
| 25 MG | Kale Leaf | 50.00 MG |
| 20 MG | Boysenberry Fruit | 40.00 MG |
| 25 MG | Pumpkin Seed | 50.00 MG |
| 20 MG | Raspberry Seed | 40.00 MG |
| 25 MG | Grape Skin SE (25%) | 50.00 MG |
| 25 MG | Blueberry Fruit | 50.00 MG |
| 35 MG | Elderberry Fruit | 70.00 MG |
| 5 MG | Apple Skin SE (5%) | 10.00 MG |
| 50 MG | Citrus Bioflavonoids (50%) | 100.00 MG |
| 20 MG | Pumpkin Fruit | 40.00 MG |
| 50 MG | Pomegranate Fruit SE (5%) | 100.00 MG |
| 30 MG | Red Bell Pepper Fruit | 60.00 MG |
| 30 MG | Tomato Fruit | 60.00 MG |
| 15 MG | Cranberry Fruit | 30.00 MG |

Women's Enzyme Digestive Capsule

| Label Claim | Ingredient Name | Daily Dosage |
|---|---|---|
| 396 MG | Enzyme Blend (Protease, peptidase, amylase, lipase, lactase, cellulose, humecellulase, alpha-galactosidase, glucoamylase, pectinase, invertase, malt diastase phytase) | 790.00 MG |
| 30 MG | Ginger Root SE (5%) | 60.00 MG |
| 25 MG | Peppermint Leaf | 50.00 MG |
| 25 MG | Chamomile Flower PE | 50.00 MG |
| 25 MG | Fennel Seed | 50.00 MG |
| 20 MG | Hawthorn Berry PE (10:1) | 40.00 MG |

The terms Aquamin Trace Mineral Complex, Mixed Tocopherols, Cranberry Fruit, High ORAC Blend, Citrus Bioflavenoids, and Enzyme Blend are or may be trademarks.

The methods of this invention comprise ingesting, twice a day, and preferably 8 to 12 hours apart, one packet of each product. Preferably, the men's product includes one tablet each of multivitamins, and of high-ORAC super food, capsule each of prostate support and one capsule of enzymes, and two tablets of multiminerals. Preferably, the women's product includes one tablet each of multivitamins and multiminerals, and of high-ORAC super food, one capsule of enzymes, and two high-calcium bone support tablets.

What is claimed is:

1. A liposome-free, ingestible product for enhancing energy in women comprising, at least one multivitamin tablet, at least one multimineral tablet, at least one calcium bone support tablet, at least one oxygen-containing food tablet, and at least one enzymes capsule, wherein said multimineral tablet comprises:

100 IU Vitamin D, 192.5 mg Calcium, 50 mg Magnesium, 0 mg Iodine, 7.5 mg Zinc, 0.1 mg Selenium, 1 mg Copper, 1 mg Manganese, 0.125 mg Chromium, 0.0375 mg Molybdenum, 37.5 mg Potassium, 1.5 mg Boron, 0.05 mg Vanadium, 6.25 mg Silica, 37.5 mg Kelp, 25 mg Seaweed powder including 34% calcium and 2.5% magnesium, 25 mg Methylsulfonylmethane (MSM)

and wherein said multivitamin tablet comprises:

5000 IU Vitamin A, 300 IU Vitamin D, 50 IU Vitamin E, 0.06 mg Vitamin K, 7.5 mg Thiamin, 7.5 mg Riboflavin, 12.5 mg Niacinamide, 12.5 mg Vitamin B6, 0.05 mg Vitamin B12, 25 mg Vitamin B5, 0.3 mg Folic Acid, 75 mg Vitamin C, 0.2 mg Biotin Mixed Tocopherols Powder including d-gammatocopherol 20%, d-alpha tocopherol 2.2%, 12.5 IU delta-tocopherol 6.6%, 12.5 mg Gamma-tocopherol, 3 mg Lutein Bead vegetable base, 0.5 mg Lycopene Bead vegetable base, 44.8 mg Dicalcium Phosphate, 5.6 mg Andrographis standard extract, 125 mg Cranberry Fruit, 20 mg Black Cohosh (2.5%) standard extract powder, 10 mg Flax Lignans, 25 mg Eleuthero Root (0.8%) standard extract, 2.5 mg Black Pepper Powder standard extract, 20 mg Crospovidone and wherein said calcium bone support tablet comprises:

112.5 mg Calcium, 12.5 mg Calcium, 12.5 mg Calcium, 12.5 mg Calcium, 87.5 mg Magnesium, 12.5 mg Magnesium, 12.5 mg Magnesium, 12.5 mg Magnesium, 5 mg Cissus, 10 mg Natural Hops Extract, 0.3504 mg Copper, 50 IU Vitamin D, 25 mg N-Acetyl-L-Cysteine and wherein said food tablet comprises:

400 mg oxygen radical absorbance capacity blend, 25 mg Broccoli Sprout, 25 mg Parsley Leaf, 25 mg Kale Leaf, 20 mg Boysenberry Fruit, 25 mg Pumpkin Seed, 20 mg Raspberry Seed, 25 mg Grape Skin (25%) standard extract, 25 mg Blueberry Fruit, 35 mg Elderberry Fruit, 5 mg Apple Skin (5%) standard extract, 50 mg Cirrus Bioflavonoids (50%), 20 mg Pumpkin Fruit, 50 mg Pomegranate Fruit (5%) standard extract, 30 mg Red Bell Pepper Fruit, 30 mg Tomato Fruit, 15 mg Cranberry Fruit and wherein said enzymes digestive capsule comprises:

395 mg Enzyme Blend, 30 mg Ginger Root (5%) standard extract, 25 mg Peppermint Leaf, 25 mg Chamomile Flower powder extract, 25 mg Fennel Seed, and 20 mg Hawthorn Berry (10:1) powder extract.

* * * * *